US005672802A

United States Patent [19]
Lutz

[11] Patent Number: 5,672,802
[45] Date of Patent: Sep. 30, 1997

[54] PROCESS FOR THE PREPARATION OF ALPHA OLEFINS

[75] Inventor: Eugene Frederick Lutz, Houston, Tex.

[73] Assignee: Shell Oil Company, Houston, Tex.

[21] Appl. No.: 618,179

[22] Filed: Mar. 19, 1996

[51] Int. Cl.$^6$ .................................................. C07C 6/04
[52] U.S. Cl. .................................... 585/643; 585/644
[58] Field of Search .................................. 585/643, 644

[56] References Cited

U.S. PATENT DOCUMENTS

| | | | |
|---|---|---|---|
| 3,261,879 | 7/1966 | Banks | 260/683 |
| 3,340,322 | 9/1967 | Heckelsberg | 260/683 |
| 3,442,970 | 5/1969 | Davison | 260/683.15 |
| 3,511,890 | 5/1970 | Reusser | 260/683 |
| 3,634,538 | 1/1972 | Steffgen | 260/683 |
| 3,637,892 | 1/1972 | McGrath | 260/683 |
| 3,647,906 | 3/1972 | Farley | 260/683 |
| 3,658,927 | 4/1972 | Crain et al. | 260/666 |
| 3,726,938 | 4/1973 | Berger | 260/683 |
| 3,760,026 | 9/1973 | Reusser et al. | 260/683 |
| 3,776,974 | 12/1973 | Gautier et al. | 260/683 |
| 3,776,975 | 12/1973 | Verbrugge et al. | 260/683 |
| 3,792,108 | 2/1974 | Arganbright | 260/683 |
| 3,829,523 | 8/1974 | Singleton | 260/683 |
| 3,865,892 | 2/1975 | Zuech | 260/683 |
| 3,872,180 | 3/1975 | Nakatomi et al. | 260/683 |
| 4,435,606 | 3/1984 | Motz et al. | 585/324 |
| 4,454,368 | 6/1984 | Banks | 585/646 |
| 4,522,936 | 6/1985 | Kubes et al. | 502/249 |
| 4,524,235 | 6/1985 | Banks et al. | 585/646 |
| 4,568,788 | 2/1986 | Kukes et al. | 585/646 |
| 4,596,786 | 6/1986 | Kukes et al. | 502/242 |
| 4,609,769 | 9/1986 | Kukes et al. | 585/646 |
| 4,629,719 | 12/1986 | Kukes et al. | 502/242 |
| 4,665,245 | 5/1987 | Quann | 585/316 |
| 4,684,760 | 8/1987 | Drake | 585/670 |
| 4,795,734 | 1/1989 | Chauvin et al. | 502/355 |
| 4,956,516 | 9/1990 | Hamilton et al. | 585/646 |
| 5,043,520 | 8/1991 | Hamilton | 585/646 |
| 5,055,628 | 10/1991 | Lin et al. | 585/647 |
| 5,098,876 | 3/1992 | Lin et al. | 502/150 |
| 5,120,896 | 6/1992 | Kemp et al. | 585/646 |

FOREIGN PATENT DOCUMENTS

| | | | |
|---|---|---|---|
| 840467 | 4/1970 | Canada | 260/696 |
| 1601567 | 11/1968 | France . | |
| 281594 | 7/1988 | Germany . | |
| 1471151 | 4/1977 | United Kingdom . | |

*Primary Examiner*—Ellen M. McAvoy
*Attorney, Agent, or Firm*—Pamela J. McCollough

[57] ABSTRACT

This invention relates a process for the preparation of an alpha olefin product having a narrow molecular weight range which comprises metathesizing an internal olefin under non-equilibrium conditions and thereby producing a lower boiling internal olefin product which is removed as formed, and a high boiling mid-chain internal olefin product, thereafter contacting and reacting the high boiling mid-chain internal olefin product with ethylene to produce an alpha olefin product having a narrow molecular weight range.

18 Claims, No Drawings

PROCESS FOR THE PREPARATION OF ALPHA OLEFINS

FIELD OF THE INVENTION

This invention relates to a process for the preparation of an alpha olefin product having a narrow molecular weight range which comprises metathesizing an internal olefin under non-equilibrium conditions and thereby producing a lower boiling internal olefin product which is removed during formation, and a high boiling mid-chain internal olefin product, thereafter contacting and reacting the mid-chain internal olefin product with ethylene and thereby producing an alpha olefin product having a narrow molecular weight range.

BACKGROUND OF THE INVENTION

Reactions of olefinic molecules in the presence of metal-containing catalysts to produce other olefinic molecules are known in the art as "metathesis" or "disproportionation" reactions. The olefin disproportionation reaction can be visualized as the breaking of two existing double bonds between the second and third carbon atoms in one molecule, and between the fourth and fifth carbon atoms in a second molecule, respectively, and the formation of two new olefins, where one new double bond is between the second and fourth carbon atoms noted and the second new double bond is between the third and fifth carbon atoms noted, respectively. A typical olefin disproportionation process is illustrated by U.S. Pat. No. 3,261,879, issued Jul. 19, 1966, to Banks, wherein two similar non-symmetrical molecules of an olefin react in the presence of certain catalysts to produce one olefin of a higher carbon number and one olefin of a lower carbon number. For example, propylene disproportionates by the process of U.S. Pat. No. 3,261,879 to produce ethylene and butylenes.

It is recognized in the industry that some molecular weight ranges of alpha olefins are more valuable than others. While there are many processes for the production of alpha olefins, most of these processes result in a wide range of olefin products. It would therefore be advantageous to have a process which would result in the production of an alpha olefin product having a selective narrow molecular weight range.

The present invention is therefore directed to a process in which internal olefins can be subjected to a metathesis step followed by an ethenolysis step in order to selectively produce a narrow molecular weight range of alpha olefins.

SUMMARY OF THE INVENTION

The present invention therefore relates to a process for the preparation of an alpha olefin product having a narrow molecular weight range which comprises: a) metathesizing an internal olefin having from about 6 to about 30 carbon atoms under non-equilibrium conditions and thereby producing a lower boiling internal olefin product which is removed during formation, and a high boiling mid-chain internal olefin product, and b) contacting and reacting the high boiling mid-chain internal olefin product with ethylene, thereby producing an alpha olefin product having a narrow molecular weight range.

DESCRIPTION OF THE PREFERRED EMBODIMENTS

In the process of the instant invention, an alpha olefin product having a narrow molecular weight range is prepared by a process which comprises metathesizing an internal olefin under non-equilibrium conditions and thereby producing a lower boiling internal olefin product which is removed during formation, and a high boiling mid-chain internal olefin product, and thereafter contacting and reacting the high boiling mid-chain internal olefin product with ethylene to produce an alpha olefin product having a narrow molecular weight range.

As used herein, the term "lower boiling" internal olefin product is used to refer to an internal olefin product having a boiling point lower than that of the starting internal olefin feed. The term "high boiling mid-chain" internal olefin product is used to refer to an internal olefin product in which the double bond is at or near the middle of the chain, as can be determined by nuclear magnetic resonance spectrometry (NMR) analysis, and which has a boiling point greater than that of the starting internal olefin feed. The term "ethenolysis", as used herein, refers to the reaction of an olefin with ethylene, or stated in another way, ethenolysis is metathesis with ethylene.

Internal olefins which are suitable for use as starting materials in the process of the present invention are internal olefins containing from about 6 to about 30 carbon atoms, and preferably from about 6 to about 24 carbon atoms. These internal olefins may be linear or branched, but are preferably linear or lightly branched. Single cut olefins or mixtures of olefins may also be used. In a particularly preferred embodiment, the internal olefin contains from about 6 to about 22 carbon atoms.

Preferred internal olefins for use in the present process are, for practical reasons of availability, the commercial olefin products in the $C_6$ to $C_{24}$ range. Internal olefins are typically produced commercially by chlorination-dehydrochlorination of paraffins, by paraffin dehydrogenation, and by isomerization of alpha-olefins. The resulting internal olefin products are substantially of linear structure. Linear internal olefin products in the $C_8$ to $C_{24}$ range are marketed by Shell Chemical Company and by Liquichemica Company. These commercial products typically contain about 70 percent by weight or more, most often about 80 percent by weight or more, linear mono-olefins in a specified carbon number range (e.g., $C_{10}$ to $C_{12}$, $C_{11}$ to $C_{15}$, $C_{12}$ to $C_{13}$, $C_{15}$ to $C_{18}$, etc.), the remainder of the product being olefin of other carbon number or carbon structure, diolefins, paraffins, aromatics, and other impurities resulting from the synthesis process. Internal olefins in the $C_6$ to $C_{22}$ range are considered most preferred for use as the olefin feed process of the present invention.

The internal olefin feed utilized in the metathesis step should be essentially free of impurities which adversely affect the reaction. The amount of internal olefin employed in the metathesis step can vary widely and will depend in part on the degree of unsaturation in the olefin feed which can be readily quantified employing known techniques. The metathesis reaction in the first step in the present invention is, however, carried out at non-equilibrium conditions, i.e, one of the products is removed as formed.

In general, any disproportionation or metathesis catalysts previously employed in such reactions can be utilized in the first step of the present process. A variety of catalysts have been employed for conducting disproportionation reactions, such as those disclosed in U.S. Pat. No. 3,340,322, issued Sep. 5, 1967; U.S. Pat. No. 3,637,892, issued Jan. 25, 1972; U.S. Pat. No. 3,760,026, issued Sep. 18, 1973; U.S. Pat. No. 3,792,108, issued Feb. 12, 1974; and U.S. Pat. No. 3,872,180, issued Mar. 18, 1975, the teachings of which are incorporated herein by reference. Among the catalysts that have been developed for disproportionation include inorganic refractory materials containing molybdenum and/or tungsten oxide. These catalysts may also contain a promoter to enhance the disproportionation catalyst activity. Elemental metal promoters selected from the group consisting of barium, magnesium, tungsten, silicon, antimony, zinc, manganese and tin are disclosed in U.S. Pat. No. 4,568,788, issued Feb. 4, 1986, U.S. Pat. No. 4,522,936, issued Jun. 11, 1985, U.S. Pat. No. 4,524,235, issued Jun. 18, 1985 and U.S. Pat. No. 4,629,719, issued Dec. 16, 1986, the teachings of which are incorporated herein by reference. In addition, organometallic compounds, such as aluminum and tin alkyls to promote solid catalysts including molybdenum and rhenium oxide for the disproportionation are disclosed in U.S. Pat. No. 4,454,368, issued Jun. 12, 1984 and U.S. Pat. No. 3,829,523, issued Aug. 13, 1974, the teachings of which are incorporated herein by reference.

While any of the aforementioned metathesis or disproportionation catalysts may be utilized in the present process, the catalyst generally utilized in the metathesis step of the present invention is one in which molybdenum or rhenium oxide are deposited on a support of silica, alumina or alumina phosphate. Prior to its use, the catalyst is typically activated by calcination carried out in a conventional manner. A particularly suitable catalyst for use in the first step of the present process is molybdenum oxide supported on alumina.

Suitable metathesis step reaction conditions, e.g., temperature, pressure, flow rates, etc., vary somewhat depending upon the specific catalyst composition, the particular feed olefin, etc. The metathesis step is typically carried out at temperatures ranging from about −10° C. to about 250° C. and at pressures in the range of about 0.1 mm Hg to about 2000 mm Hg. The metathesis step is usually effected in a liquid phase and if desired, liquid reaction diluents are utilized. Examples of suitable diluents are saturated hydrocarbons. If the diluent is present, it is present in amounts up to 20 moles of diluent per mole of internal olefinic reactant.

In the first step or metathesis step of the process, the starting internal olefin feed is subjected to metathesis with the resulting products being a lower boiling internal olefin product which is removed as it is formed by reactive distillation, and a high boiling mid-chain internal olefin product. It is essential that the lower boiling internal olefin product be removed during formation in order to obtain the greatest amount possible of the desired high boiling mid-chain olefin product which can then be converted by ethenolysis into the desired alpha olefin product having a narrow molecular weight range. If the lower boiling internal olefin product is not removed as it is formed, an equilibrium distribution of products will be formed and the high boiling mid-chain olefin product will be formed in lesser amounts.

Following the metathesis step, the high boiling mid-chain olefin product is separated by means of distillation from any unconverted starting internal olefin feed. Any unconverted starting olefin feed material is then recycled in order to maximize use of the internal olefin feed.

The high boiling mid-chain internal olefin product from the metathesis step is then subjected to a second step, an ethenolysis step in which the high boiling mid-chain internal olefin product is contacted and reacted with ethylene in the presence of an ethenolysis catalyst to form an alpha olefin product having a narrow molecular weight range.

Suitable ethenolysis catalysts, which are generally any ethenolysis catalysts known to be utilized in the reaction of ethylene with an olefin can be utilized in the second step of the present process. However, the ethenolysis catalyst suitable for use in the present invention should have little, if any, double bond isomerization activity, as the presence of such would result in side reactions leading to isomerization of alpha olefins to internal olefins thus resulting in the production of lower amounts of alpha olefins. Particularly suitable for use in the ethenolysis step of the present invention is a rhenium-on-alumina catalyst such as that disclosed in U.S. Pat. No. 3,647,906, issued Mar. 7, 1972, the teachings of which are incorporated herein by reference. Also suitable would be a heterogeneous molybdenum oxide catalyst such as that disclosed in U.S. Pat. No. 3,658,927, issued Apr. 25, 1972, the teaching of which are incorporated herein by reference. Any of the disproportionation catalysts mentioned with respect to the first step of the present process may also be utilized in this second step provided they have little or no double bond isomerization activity.

Suitable ethenolysis step reaction conditions, e.g., temperature, pressure, flow rates, etc., vary somewhat depending upon the specific catalyst composition, the particular feed olefin, etc. The ethenolysis step is typically carried out at temperatures ranging from about −10° C. to about 250° C. and at pressures in the range of about 25 psig to about 1500 psig. The ethenolysis step is usually effected in a liquid phase and if desired, liquid reaction diluents are utilized. Examples of suitable diluents are hydrocarbons free which are from aliphatic unsaturation, such as cyclic or alicyclic alkanes which can be readily separated from alpha olefin product and mid-chain olefin feed by conventional means, such as, for example, distillation. If the diluent is added, it is present in amounts up to 20 moles of diluent per mole of mid-chain internal olefinic reactant.

By way of illustration, the process of the present invention can be used as follows to metathesize a $C_{11/12}$ substantially linear internal olefin (IO) to produce a $C_{13/20}$ high boiling mid-chain internal olefin (MCO) and a $C_{3/10}$ internal olefin which is removed as formed and thereafter ethenolyze the $C_{13/20}$ high boiling mid-chain internal olefin (MCO) to produce a linear alpha olefin product having a narrow molecular weight range, i.e., $C_7$ to $C_{11}$:

a) $C_{11/12}$ IO→$C_{13/20}$ MCO+$C_{3/10}$ IO (Metathesis)
b) $C_{13/20}$ MCO+$C_2H_4$→$C_{7/11}$ AO (Ethenolysis)

The two-step process of the invention can be carried out either batchwise or continuously, using a fixed catalyst bed, or a stirrer equipped reactor or other mobile catalyst contacting process as well as any other well known contacting technique. With a fixed bed reactor, for example, continuous flow operation for the metathesis step is at pressures in the range of about 0.1 mm Hg to about 2000 mm Hg, preferably about 4 mm Hg to about 760 mm Hg, with catalysts having densities ranging from about 0.3 gram per cc to about 2.0 gram per cc and surface areas greater than about 100 m²/g, and at temperatures in the range of about −10° C. to about 250° C., preferably at about 30° C. to about 150° C., at volume hourly space velocities in the range of about 0.1 to about 10.0 parts by volume of mid-chain internal olefin feed per part by volume of catalyst per hour are suitable.

The narrow range alpha olefin products prepared according to the present invention can be utilized in a wide variety of applications. For example, the olefins can be used as comonomers for the manufacture of linear low density polyethylene, or the olefins can be oligomerized to synthetic lubricants. Higher molecular weight olefins are useful as intermediates in the preparation of surfactants.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

Illustrative Embodiments

Catalyst A

Catalyst A, utilized in the examples below, was prepared by comulling 125.3 g of alumina with 6.0 g of molybdenum trioxide in the presence of an aqueous acetic solution made up by dissolving 5.6 g of glacial acetic acid in 101.5 g of deionized water. After mulling for 30–45 minutes, the resulting paste was extruded to produce 1.2 mm trilobes. Following drying at 121° C. for several hours, the extrudate was calcined at 510°–593° C. for 2 hours.

Using a conventional dry pore volume impregnation technique, 100 g of trilobe extrudate was impregnated with 70 cc of an aqueous solution containing 8.0 g of ammonium dimolybdate. After aging for 2 hours, the catalyst was dried at 121° C. for 2–3 hours, and then calcined at 427°–538° C. for 2 hours.

Catalyst B

Catalyst B utilized in the examples below was prepared using a conventional dry pore volume impregnation technique. A solution suitable for impregnating 150.0 grams of calcined alumina support with a pore volume of 0.8–1.0 cc/g was prepared as follows. An impregnation solution was made by combining 28.13 grams of ammonium perrhenate and 220.10 grams of deionized water. After adding the entire solution to the alumina support in several small portions with continuous rotary agitation, the impregnated support was dried in a Rotovac at 25° to 121° C. with vacuum decreasing for 360 mm Hg to 4 mm Hg and then calcined in air by heating from 37° to 500° C. at 2°/min and holding at 500° C. for 2 hours.

EXAMPLE 1 a) Metathesis Step

In a nitrogen glove-box, 30 ccs of Catalyst A was added to glass reactor having a glass wool plug to hold the catalyst in place. After the catalyst was loaded, a round bottomed flask was attached to the bottom of the tube while the top was sealed with a stopper to prevent air intrusion when the tube was removed from the glove-box. Outside of the glove-box, a three-necked flask was attached to the bottom and nitrogen was passed into the column via an oil bubbler such that the pressure could not exceed atmospheric pressure. With a nitrogen flow, the stopper at the top was removed and replaced with a thermocouple that extended half of the way into the catalyst bed. The thermocouple passed through a metal 24/40 joint that was fitted into a metal pipe such that a feed inlet and a vacuum outlet were available to add olefin to the top of the catalyst bed and to pull a vacuum about the feed inlet.

When the catalyst bed assembly was complete, a $C_{8/9/10}$ internal olefin was pumped at a rate of 30 cc/hour from an Isco pump into the top of the reactor. Pressure at the top and bottom of the reactor was about 760 mm Hg and warm oil at 119° C. was circulated through the reactor jacket. Approximately two hours after liquid break-through was achieved, a spot sample was collected in an ice bath for gas chromatography analysis. At the end of the run period, all product at the bottom of the reactor and all low boiling olefin in the cold trap was collected, weighed, and analyzed by gas chromatography. After the mid-chain olefin was recovered by distillation, NMR was used to determine that the double bond was at or near the center of the olefin chain.

Results obtained from the metathesis step are presented in Table I.

b) Ethenolysis Step

In a nitrogen glove-box, 15 ccs of Catalyst B was charged to a metal, fixed bed, jacketed reactor. The catalyst was held in place with an inverted metal screen basket at the bottom of the tube. A thermocouple was extended from the top of the reactor to the center of the catalyst bed. The top of the fixed bed reactor was fitted with a feed inlet line, pressure relief valve, thermocouple, and pressure transducer. Both the top and the bottom had block valves so that the reactor could be sealed in the glove-box after catalyst loading. After the reactor was removed from the glove-box, it was equipped with liquid and gas feed lines for the inlet at the top and a Grove back-pressure regulator at the bottom for pressure control. Circulating hot oil was used to heat the reactor. When the reactor assembly was complete, it was tested for leaks at 560 psig nitrogen.

The fixed bed reactor was started by pumping the liquid $C_{11/15}$ high boiling mid-chain internal olefin product from the metathesis step from an Isco piston pump downflow. When liquid break-through was achieved, ethylene was introduced and pressure was raised to 300 psig by means of the back-pressure regulator. Oil was circulated through the reactor jacket at about 32° C. As the reaction exothermed, a plastic bag of ice was inserted into the oil bath so that the temperature in the middle of the catalyst was maintained at 32±/°C. Product was collected in an ice cooled round bottomed flask that vented to a dry ice cooled cold trap. The first spot sample to check conversion of the high boiling mid-chain internal olefin was taken about two hours after ethylene was added to the reactor. Ethylene flow through the reactor was monitored regularly and maintained at about 30–40 ccs/minute. At the end of a day's run, conversion and selectivity were determined by gas chromatography analysis. Linear alpha olefin content of product was determined by gas chromatography analysis before and after hydrogenation.

The results obtained from the ethenolysis step are presented in Table II.

EXAMPLE 2 a) Metathesis Step

In a nitrogen glove-box, 10 ccs of Catalyst B was added to glass reactor having a glass wool plug to hold the catalyst in place. After the catalyst was loaded, a round bottomed flask was attached to the bottom of the tube while the top was sealed with a stopper to prevent air intrusion when the tube was removed from the glove-box. Outside of the glove-box, a three-necked flask was attached to the bottom and nitrogen was passed into the column via an oil bubbler such that the pressure could not exceed atmospheric pressure. With a nitrogen flow, the stopper at the top was removed and replaced with a thermocouple that extended half of the way into the catalyst bed. The thermocouple passed through a metal 24/40 joint that was fitted into a metal pipe such that a feed inlet and a vacuum outlet were available to add olefin to the top of the catalyst bed and to pull a vacuum about the feed inlet.

When the catalyst bed assembly was complete, a $C_{11/12}$ internal olefin was pumped at a rate of 10 cc/hour from an Isco pump into the top of the reactor. Vacuum was set at about 4–5 mm Hg at the top and bottom of the reactor, and warm oil at 45° C. was circulated through the reactor jacket. Approximately two hours after liquid break-through was achieved, a spot sample was collected in an ice bath for gas chromatography analysis. At the end of the run period, all product at the bottom of the reactor and all low boiling olefin in the cold trap was collected, weighed, and analyzed by gas chromatography. After the mid-chain olefin was recovered by distillation, NMR was used to determine that the double bond was at or near the center of the olefin chain.

Results obtained from the metathesis step are presented in Table I.

b) Ethenolysis Step

In a nitrogen glove-box, 20 ccs of Catalyst B was charged to a metal, fixed bed, jacketed reactor. The catalyst was held in place with an inverted metal screen basket at the bottom of the tube. A thermocouple was extended from the top of the reactor to the center of the catalyst bed. The top of the fixed bed reactor was fitted with a feed inlet line, pressure relief valve, thermocouple, and pressure transducer. Both the top and the bottom had block valves so that the reactor could be sealed in the glove-box after catalyst loading. After the reactor was removed from the glove-box, it was equipped with liquid and gas feed lines for the inlet at the top and a Grove back-pressure regulator at the bottom for pressure control. Circulating hot oil was used to heat the reactor. When the reactor assembly was complete, it was tested for leaks at 560 psig nitrogen.

The fixed bed reactor was started by pumping the liquid $C_{13/20}$ high boiling mid-chain internal olefin product from the metathesis step from an Isco piston pump downflow. When liquid break-through was achieved, ethylene was introduced and pressure was raised to 300 psig by means of the back-pressure regulator. Oil was circulated through the reactor jacket at about 32° C. As the reaction exothermed, a plastic bag of ice was inserted into the oil bath so that the temperature in the middle of the catalyst was maintained at 32°±2° C. Product was collected in an ice cooled round bottomed flask that vented to a dry ice cooled cold trap. The first spot sample to check conversion of the high boiling mid-chain internal olefin was taken about two hours after ethylene was added to the reactor. Ethylene flow through the reactor was monitored regularly and maintained at about 30–40 ccs/minute. At the end of a day's run, conversion and selectivity were determined by gas chromatography analysis. Linear alpha olefin content of product was determined by gas chromatography analysis before and after hydrogenation.

The results obtained from the ethenolysis step are presented in Table II.

Comparative Example A

The ethenolysis step was carried out in a manner similar to the ethenolysis step in Example 2 above except that a $C_{18}$ internal olefin having a random double bond distribution was used instead of the $C_{13/20}$ high boiling mid-chain internal olefin product.

The results obtained from the ethenolysis step are presented in Table II.

EXAMPLE 3 a) Metathesis Step

In a nitrogen glove-box, 10 ccs of Catalyst A was added to glass reactor having a glass wool plug to hold the catalyst in place. After the catalyst was loaded, a round bottomed flask was attached to the bottom of the tube while the top was sealed with a stopper to prevent air intrusion when the tube was removed from the glove-box. Outside of the glove-box, a three-necked flask was attached to the bottom and nitrogen was passed into the column via an oil bubbler such that the pressure could not exceed atmospheric pressure. With a nitrogen flow, the stopper at the top was removed and replaced with a thermocouple that extended half of the way into the catalyst bed. The thermocouple passed through a metal 24/40 joint that was fitted into a metal pipe such that a feed inlet and a vacuum outlet were available to add olefin to the top of the catalyst bed and to pull a vacuum about the feed inlet.

When the catalyst bed assembly was complete, a $C_{11/12}$ internal olefin was pumped at a rate of 10 cc/hour from an Isco pump into the top of the reactor. Vacuum was set at about 130 mm Hg at the top and bottom of the reactor, and warm oil at about 120° C. was circulated through the reactor jacket. Approximately two hours after liquid break-through was achieved, a spot sample was collected in an ice bath for gas chromatography analysis. At the end of the run period, all product at the bottom of the reactor and all low boiling olefin in the cold trap was collected, weighed, and analyzed by gas chromatography. After the mid-chain olefin was recovered by distillation, NMR was used to determine that the double bond was at or near the center of the olefin chain.

Results obtained from the metathesis step are presented in Table I.

b) Ethenolysis Step

In a nitrogen glove-box, 20 ccs of Catalyst A was charged to a metal, fixed bed, jacketed reactor. The catalyst was held in place with an inverted metal screen basket at the bottom of the tube. A thermocouple was extended from the top of the reactor to the center of the catalyst bed. The top of the fixed bed reactor was fitted with a feed inlet line, pressure relief valve, thermocouple, and pressure transducer. Both the top and the bottom had block valves so that the reactor could be sealed in the glove-box after catalyst loading. After the reactor was removed from the glove-box, it was equipped with liquid and gas feed lines for the inlet at the top and a Grove back-pressure regulator at the bottom for pressure control. Circulating hot oil was used to heat the reactor. When the reactor assembly was complete, it was tested for leaks at 560 psig nitrogen.

The fixed bed reactor was started by pumping the liquid $C_{13/20}$ high boiling mid-chain internal olefin product from the metathesis step from an Isco piston pump downflow. When liquid break-through was achieved, ethylene was introduced and pressure was raised to 300 psig by means of the back-pressure regulator. Oil was circulated through the reactor jacket at about 80° C. Product was collected in an ice cooled round bottomed flask that vented to a dry ice cooled cold trap. A spot sample was collected to determine high boiling mid-chain external olefin conversion and linear alpha olefin selectivity about three hours after the temperature reached 80° C. Ethylene flow through the reactor was monitored regularly and maintained at about 30–40 ccs/minute. Linear alpha olefin content of product was determined by gas chromatography analysis before and after hydrogenation.

The results obtained from the ethenolysis step are presented in Table II.

EXAMPLE 4 a) Metathesis Step

In a nitrogen glove-box, 30 ccs of Catalyst B was added to glass reactor having a glass wool plug to hold the catalyst in place. After the catalyst was loaded, a round bottomed flask was attached to the bottom of the tube while the top was sealed with a stopper to prevent air intrusion when the tube was removed from the glove-box. Outside of the glove-box, a three-necked flask was attached to the bottom and nitrogen was passed into the column via an oil bubbler such that the pressure could not exceed atmospheric pressure. With a nitrogen flow, the stopper at the top was removed and replaced with a thermocouple that extended half of the way into the catalyst bed. The thermocouple passed through a metal 24/40 joint that was fitted into a metal pipe such that a feed inlet and a vacuum outlet were available to add olefin to the top of the catalyst bed and to pull a vacuum about the feed inlet.

When the catalyst bed assembly was complete, a $C_{14/17}$ internal olefin was pumped at a rate of 30 cc/hour from an Isco pump into the top of the reactor. Vacuum was set at about 1–2 mm Hg at the top and bottom of the reactor, and warm oil at 45° C. was circulated through the reactor jacket. Approximately two and one-half hours after liquid break-through was achieved, a spot sample was collected in an ice bath for gas chromatography analysis. At the end of the run period, all product at the bottom of the reactor and all low boiling olefin in the cold trap was collected, weighed, and analyzed by gas chromatography. After the mid-chain olefin was recovered by distillation, NMR was used to determine that the double bond was at or near the center of the olefin chain.

Results obtained from the metathesis step are presented in Table I.

b) Ethenolysis Step

In a nitrogen glove-box, 15 ccs of Catalyst B was charged to a metal, fixed bed, jacketed reactor. The catalyst was held in place with an inverted metal screen basket at the bottom of the tube. A thermocouple was extended from the top of the reactor to the center of the catalyst bed. The top of the fixed bed reactor was fitted with a feed inlet line, pressure relief valve, thermocouple, and pressure transducer. Both the top and the bottom had block valves so that the reactor could be sealed in the glove-box after catalyst loading. After the reactor was removed from the glove-box, it was equipped with liquid and gas feed lines for the inlet at the top and a Grove back-pressure regulator at the bottom for pressure control. Circulating hot oil was used to heat the reactor. When the reactor assembly was complete, it was tested for leaks at 560 psig nitrogen.

The fixed bed reactor was started by pumping the liquid $C_{18/25}$ high boiling mid-chain internal olefin product from the metathesis step from an Isco piston pump downflow. When liquid break-through was achieved, ethylene was introduced and pressure was raised to 300 psig by means of the back-pressure regulator. Oil was circulated through the reactor jacket at about 32° C. As the reaction exothermed, a plastic bag of ice was inserted into the oil bath so that the temperature in the middle of the catalyst was maintained at 31°±1° C. Product was collected in an ice cooled round bottomed flask that vented to a dry ice cooled cold trap. The first spot sample to check conversion of the high boiling mid-chain internal olefin was taken about two hours after ethylene was added to the reactor. Ethylene flow through the reactor was monitored regularly and maintained at about 30–40 ccs/minute. At the end of a day's run, conversion and selectivity were determined by gas chromatography analysis. Linear alpha olefin content of product was determined by gas chromatography analysis before and after hydrogenation.

The results obtained from the ethenolysis step are presented in Table II.

TABLE I

Mid-Chain Olefins (MCO) via Fixed Bed Reaction LHSV, 1.0

| Ex. No. | Internal Olefin Feed | Catalyst | Temp. °C. | Vac., mm Hg | Conv. % wt | MCO Product | Double Bond at Mid-chain, % wt | Sel. % wt |
|---|---|---|---|---|---|---|---|---|
| 1 | $C_{8/9/10}$ | A | 119 | ~760 | 62.0 | $C_{11/15}$ | 86 | 77 |
| 2 | $C_{11/12}$ | B | 45 | 5–5 | 88.6 | $C_{13/20}$ | 99 | 75 |
| 3 | $C_{11/12}$ | A | 120 | 130 | 85.6 | $C_{13/20}$ | 97 | 76 |
| 4 | $C_{14/17}$ | B | 45 | 1–2 | 55.5 | $C_{18/25}$ | 99 | 60 |

TABLE II

Linear Alpha Olefins by Ethenolysis of MCO Ethylene Pressure, 300 psig

| Ex. No. | MCO | Cat. | LHSV | Temp. °C. | Conv. % wt | LAO Selectivity, % wt ||||||| LAO Content, % wt[b] |
|---|---|---|---|---|---|---|---|---|---|---|---|---|---|
| | | | | | | ≤$C_6$ | $C_{7/8}$ | $C_9$ | $C_{10/11}$ | $C_{12}$ | $C_{13/14}$ | $C_{15/16}$ | |
| 1 | $C_{15/16}$ | B | 1.0 | 32 | 65 | 24.1 | 46.2 | 20.9 | 8.7 | | | | 93–97[c] |
| 2 | $C_{13/20}$ | B | 1.0 | 32 | 45 | 5.0 | 19.0 | 16.9 | 57.2 | 1.9 | | | 97–98[d] |
| Comp. Ex. A | $C_{18}IO$[a] | B | 1.0 | 50 | 50 | 1.8 | 4.8 | 3.3 | 8.3 | 4.6 | 12.2 | 17.7 | |
| 3 | $C_{13/20}$ | A | 0.5 | 80 | 40 | 4.6 | 20.8 | 18.5 | 49.0 | 7.0 | | | 90[e] |
| 4 | $C_{18/25}$ | B | 1.0 | 32 | 30 | 3.7 | 9.1 | 8.5 | 25.0 | 13.9 | 25.6 | 14.2 | 96–97[f] |

[a] Internal olefin having a random double bond distribution.
[b] Purity of principal products produced.
[c] Principal product : $C_{7/8}$
[d] Principal product : $C_{9/10/11}$
[e] Principal product : $C_{9/10/11}$
[f] Principal product : $C_{10/11/12}$ Discussion of the Results The key step in the present invention is the conversion of random internal olefins, which are non-symmetrical, i.e., olefins having different size alkyl groups attached to the double bond, to mid-chain olefins, which are symmetrical, i.e., olefins having about the same size alkyl groups attached to the double bond. As can be seen in Table II, Example 2 shows that ethenolysis of a $C_{13/20}$ mid-chain olefin produce a $C_{7/12}$ alpha olefin selectivity of 95.0% by weight. By contrast, as can also be seen in Table II, Comparative Example A shows that the ethenolysis of a random $C_{18}$ internal olefin results in the production of olefins in the range of from $C_3$ to $C_{33}$, and gives a $C_{7/12}$ alpha olefin selectivity of 21.0% by weight. The production of the mid-chain olefins, as summarized in Table I, was accomplished by metathesizing random internal olefins under non-equilibrium, reactive distillation conditions where olefins having a lower boiling point than the starting internal olefin feed were flashed as formed, thus leaving higher boiling, more symmetrical mid-chain olefins. It is also important to note that the catalysts used, particularly those utilized in the ethenolysis step, should not have significant double bond isomerization activity as catalysts containing such activity will result in much poorer product selectivity and purity.

I claim as my invention:

1. A process for the preparation of a alpha olefin product having a narrow molecular weight range which comprises: a) metathesizing an internal olefin having in the range of from about 6 to about 30 carbon atoms under non-equilibrium conditions and thereby producing a lower boiling internal olefin product which is removed as formed, and a high boiling mid-chain internal olefin product, and b) contacting and reacting the high boiling mid-chain internal olefin product with ethylene, thereby producing an alpha olefin product having a narrow molecular weight range.

2. The process of claim 1 wherein said internal olefin has in the range of from about 6 to about 25 carbon atoms.

3. The process of claim 2 wherein said internal olefin has in the range of from about 6 to about 22 carbon atoms.

4. The process of claim 1 wherein step a) is carried out in the presence of a metathesis catalyst.

5. The process of claim 4 wherein said metathesis catalyst comprises at least one of molybdenum or rhenium supported on an inorganic oxide support.

6. The process of claim 1 wherein said step a) is carried out at a temperature in the range of from about −10° C. to about 250° C. and a pressure in the range of from about 0.1 mm Hg to about 2000 mm Hg.

7. The process of claim 1 wherein step b) is carried out in the presence of a ethenolysis catalyst.

8. The process of claim 7 wherein said ethenolysis catalyst comprises at least one of molybdenum or rhenium supported on an inorganic oxide support.

9. The process of claim 1 wherein step b) is carried out at a temperature in the range of from about −10° C. to about 250° C. and a pressure in the range of from about 25 psig to about 1500 psig.

10. An alpha olefin product having a narrow molecular weight range prepared by a process which comprises: a) metathesizing an internal olefin having in the range of from about 6 to about 30 carbon atoms under non-equilibrium conditions and thereby producing a lower boiling internal olefin product which is removed as formed, and a high boiling mid-chain internal olefin product, and b) contacting and reacting the high boiling mid-chain internal olefin product with ethylene, thereby producing an alpha olefin product having a narrow molecular weight range.

11. The alpha olefin product of claim 10 wherein in step a), said internal olefin has in the range of from about 6 to about 25 carbon atoms.

12. The alpha olefin product of claim 11 wherein said internal olefin has in the range of from about 6 to about 22 carbon atoms.

13. The alpha olefin product of claim 11 wherein step a) is carried out in the presence of a metathesis catalyst.

14. The alpha olefin product of claim 13 wherein said metathesis catalyst comprises at least one of molybdenum or rhenium supported on an inorganic oxide support.

15. The alpha olefin product of claim 10 wherein said step a) is carried out at a temperature in the range of from about −10° C. to about 250° C. and a pressure in the range of from about 0.1 mm Hg to about 2000 mm Hg.

16. The alpha olefin product of claim 10 wherein step b) is carried out in the presence of a ethenolysis catalyst.

17. The alpha olefin product of claim 16 wherein said ethenolysis catalyst comprises at least one of molybdenum or rhenium supported on an inorganic oxide support.

18. The alpha olefin product of claim 10 wherein step b) is carried out at a temperature in the range of from about −10° C. to about 250° C. and a pressure in the range of from about 25 psig to about 1500 psig.

* * * * *